(12) United States Patent
Shibuya et al.

(10) Patent No.: US 7,459,552 B2
(45) Date of Patent: *Dec. 2, 2008

(54) METHOD FOR PRODUCING CYCLIC DIAMINE DERIVATIVE OR SALT THEREOF

(75) Inventors: Kimiyuki Shibuya, Tokorozawa (JP); Tadaaki Ohgiya, Tokorozawa (JP); Toru Miura, Higashimurayama (JP)

(73) Assignee: Kowa Co., Ltd., Nagoya-shi (JP)

( * ) Notice: Subject to any disclaimer, the term of this patent is extended or adjusted under 35 U.S.C. 154(b) by 323 days.

This patent is subject to a terminal disclaimer.

(21) Appl. No.: 10/558,197

(22) PCT Filed: May 27, 2004

(86) PCT No.: PCT/JP2004/007258

§ 371 (c)(1),
(2), (4) Date: Nov. 25, 2005

(87) PCT Pub. No.: WO2004/106323

PCT Pub. Date: Dec. 9, 2004

(65) Prior Publication Data

US 2006/0293519 A1 Dec. 28, 2006

(30) Foreign Application Priority Data

May 28, 2003 (JP) .............................. 2003-150971

(51) Int. Cl.
| C07D 239/00 | (2006.01) |
| C07D 239/02 | (2006.01) |
| C07D 241/04 | (2006.01) |
| C07D 243/00 | (2006.01) |
| C07D 295/00 | (2006.01) |

(52) U.S. Cl. ..................... 540/553; 544/242; 544/358
(58) Field of Classification Search .................. None
See application file for complete search history.

(56) References Cited

U.S. PATENT DOCUMENTS

| 6,969,711 | B2 | 11/2005 | Shibuya et al. |
| 6,998,486 | B2 | 2/2006 | Shibuya et al. |
| 2004/0176593 | A1 | 9/2004 | Shibuya et al. |
| 2005/0020606 | A1 | 1/2005 | Shibuya et al. |
| 2006/0293519 | A1 | 12/2006 | Shibuya et al. |

OTHER PUBLICATIONS

U.S. Appl. No. 10/558,197, filed Nov. 25, 2005, Shibuya, et al.
U.S. Appl. No. 10/535,705, filed May 20, 2005, Shibuya et al.
Kubota, Toshio et al., Facile Synthesis of Unsymmetrical Sulfides Using Bis (2,2,2-Trifluoroethoxy) Triphenylphosphorane, Chemistry LettersNo. 7, pp. 845-846, 1979.
Vader, Jan et al., Stereoselective Syntheses of 2-Substituted Perhydrofuro (2, 3-b) furans, Tetrahedron, vol. 44, No. 9, pp. 2663-2674, 1988.
U.S. Appl. No. 11/631,397, filed Dec. 29, 2006, Shibuya et al.

*Primary Examiner*—James O. Wilson
*Assistant Examiner*—Noble Jarrell
(74) *Attorney, Agent, or Firm*—Oblon, Spivak, McClelland, Maier & Neustadt, P.C.

(57) ABSTRACT

The present invention is directed to a method for producing a cyclic diamine compound (3) or a salt thereof through the following scheme:

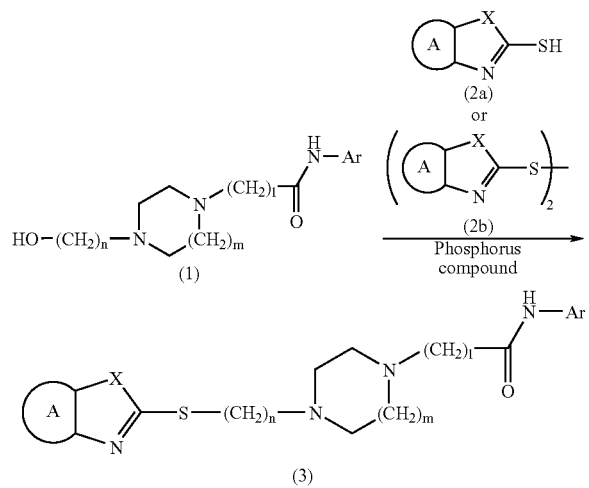

(wherein Ar represents a phenyl group, a pyridyl group, or a pyrimidinyl group, any of which may have a substituent; X represents NH, S, or O; ring A represents a benzene ring or a pyridine ring, which may have a substituent; l represents an integer of 1 or 2; m represents an integer of 1 or 2; and n represents an integer of 1 to 6). The method enables synthesis of a cyclic diamine compound (3) or a salt thereof, which serves as an ACAT inhibitor, in an industrially useful manner.

18 Claims, No Drawings

METHOD FOR PRODUCING CYCLIC DIAMINE DERIVATIVE OR SALT THEREOF

TECHNICAL FIELD

The present invention relates to a method for producing a cyclic diamine derivative or a salt thereof, which serves as an acyl-coenzyme A cholesterol acyltransferase (ACAT) inhibitor.

BACKGROUND ART

Having focused on a specific type of ACAT that is present in the vascular wall, the present inventors previously studied a substance which selectively inhibits the ACAT, and found that, among azole compounds having a cyclic diamine structure, cyclic diamine derivatives represented by the following formula (3):

[F1]

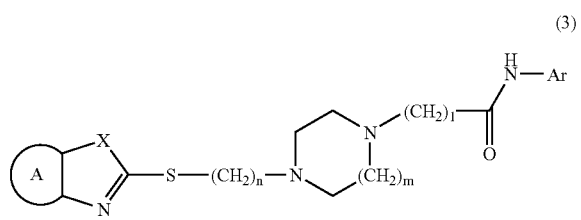

(3)

(wherein Ar represents a phenyl group, a pyridyl group, or a pyrimidinyl group which may have a substituent; X represents NH, S, or O; and ring A represents a benzene ring or a pyridine ring which may have a substituent; l is an integer of 1 or 2; m is an integer of 1 or 2; and n is an integer of 1 to 6) and salts thereof are useful therapeutic drugs for hyperlipidemia and arteriosclerosis by virtue of less side effect, excellent water-solubility, and peroral absorbability. They filed an international patent application on the basis of these findings (Patent Document 1).

The above patent application discloses a method for producing azole compounds (3') including the cyclic diamine derivatives represented by the above formula (3). According to the method, as shown in the following reaction scheme:

[F2]

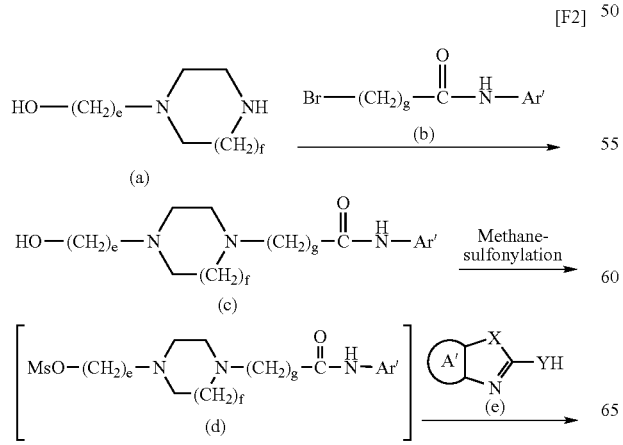

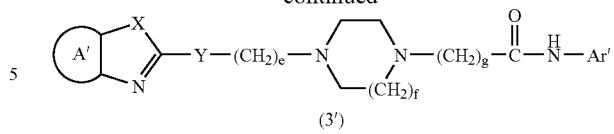

(3')

(wherein Ar' represents an aryl group which may have a substituent; X represents NH, S, or O; ring A' represents a benzene ring, a pyridine ring, or a similar ring, any of which may have a substituent; Y represents S, O, or a similar element; e is an integer of 1 to 15; f is an integer of 1 or 2; and g is an integer of 1 to 3), a 1-(hydroxyalkyl)piperazine (a) is reacted with a haloalkylamide compound (b), to thereby produce an alcohol derivative (c). The hydroxyl group of the alcohol derivative is transformed into a leaving group such as a methanesulfonyloxy group, to thereby yield a compound (d), followed by reacting with a compound (e), to thereby produce an azole compound (3').

However, the above method has drawbacks. For example, formation of the thioether bond during transformation of the alcohol derivative (c) to the cyclic diamine derivative (3') requires two steps; i.e., methanesulfonylation and condensation with a compound (e). Since the methanesulfonyloxy species (d) formed in the first step is highly reactive, the final product yield decreases due to by-products formed during posttreatment after the first step or condensation with the compound (e).

Patent Document 1: Pamphlet of International Publication WO 98/54153

DISCLOSURE OF THE INVENTION

Problems to be Solved by the Invention

An object of the present invention is to provide an industrially useful method for synthesizing a cyclic diamine derivative (3) or a salt thereof which serves as an ACAT inhibitor.

Means for Solving the Problems

Under such circumstances, the present inventors have conducted extensive studies, and have found that a cyclic diamine derivative (3) or a salt thereof can be produced at high yield and high purity through a single step in which a compound (1) is reacted with a thiol derivative (2a) or (2b) in the presence of a phosphorus compound, as shown in the following scheme:

[F3]

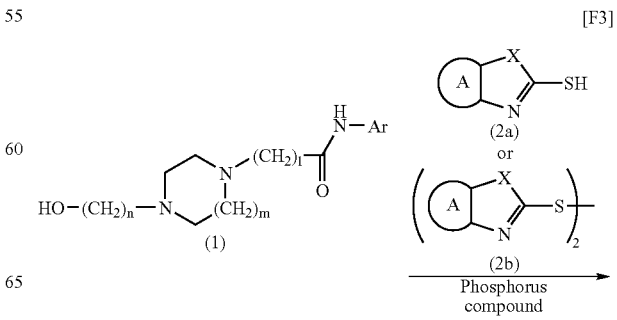

-continued

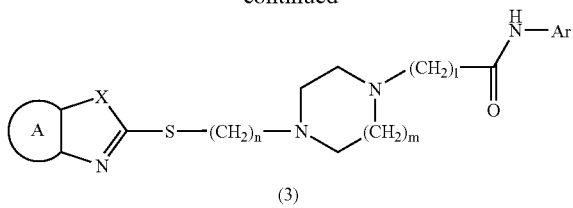

(3)

(wherein Ar represents a phenyl group, a pyridyl group, or a pyrimidinyl group, any of which may have a substituent; X represents NH, S, or O; ring A represents a benzene ring or a pyridine ring, which may have a substituent; l represents an integer of 1 or 2; m represents an integer of 1 or 2; and n represents an integer of 1 to 6). The present invention has been accomplished on the basis of this finding.

Accordingly, the present invention provides a method for producing a cyclic diamine derivative (3) or a salt thereof, characterized in that the method comprising reacting a compound (1) with a thiol derivative (2a) or (2b) in the presence of a phosphorus compound.

EFFECTS OF THE INVENTION

According to the present invention, cyclic diamine derivatives (3) and salts thereof, which are useful for drugs, can be produced at high yield and high purity in an industrially useful manner.

BEST MODES FOR CARRYING OUT THE INVENTION

The present invention will next be described in more detail.

The phenyl group, pyridyl group, and pyrimidinyl group, each represented by Ar in formula (1) or (3), may have a substituent. Examples of the substituent which can replace a ring hydrogen atom include lower alkyl, lower alkoxy-lower alkyl, halogen-substituted lower alkyl, lower alkoxy, halogen-substituted lower alkoxy, lower alkoxy-lower alkoxy, lower alkoxycarbonyl-lower alkoxy, lower alkylthio, lower alkylsulfinyl, lower alkylsulfonyl, lower alkylcarbonyloxy, lower alkylsulfonyloxy, di-lower alkoxyphosphonyloxy, and lower alkylcarbonyl groups, a halogen atom, nitro, sulfonamido, mono- or di-lower alkylamino, cyclic amino, and lower alkylenedioxy groups. Of these, lower alkyl, lower alkoxy, halogen-substituted lower alkoxy, lower alkoxy-lower alkoxy, lower alkoxycarbonyl-lower alkoxy, lower alkylthio, lower alkylcarbonyloxy, lower alkylsulfonyloxy, di-lower alkoxyphosphonyloxy, nitro, and mono- or di-lower alkylamino groups are preferred.

The benzene ring or pyridine ring represented by ring A in formula (2a), (2b), or (3) may have a substutuent. Examples of the substituent which can replace a ring hydrogen atom include lower alkyl, lower alkoxy-lower alkyl, halogen-substituted lower alkyl, lower alkoxy, halogen-substituted lower alkoxy, lower alkoxy-lower alkoxy, lower alkoxycarbonyl-lower alkoxy, aryl lower alkoxy, lower alkylthio, lower alkylsulfinyl, lower alkylsulfonyl, lower alkylcarbonyl, and lower alkoxycarbonyl groups, a halogen atom, nitro, cyano, sulfonamido, mono- or di-lower alkylamino, mono- or di-lower alkylamino-lower alkyl, and lower alkylenedioxy groups, and a heterocyclic residue. Of these, for example, lower alkyl, lower alkoxy-lower alkyl, halogen-substituted lower alkyl, lower alkoxy, lower alkylthio, lower alkylsulfonyl, lower alkylcarbonyl, and lower alkoxycarbonyl groups, a halogen atom, nitro group, and a heterocyclic residue are preferred.

The "lower alkyl" included in the aforementioned substituents is preferably a linear, branched, or cyclic alkyl group having 1 to 6 carbon atoms. Examples include methyl, ethyl, propyl, isopropyl, butyl, isobutyl, cyclopropyl, cyclobutyl, cyclopentyl, and cyclohexyl groups. Examples of the lower alkyl moiety of the "lower alkoxy" is include linear, branched, and cyclic alkyl groups each having 1 to 6 carbon atoms. Examples of the "lower alkoxy" include methoxy, ethoxy, n-propoxy, isopropoxy, n-butoxy, isobutoxy, cyclopropylmethoxy, cyclobutoxy, cyclopentyloxy, and cyclohexyloxy groups. Examples of the halogen atom serving as the "substituting halogen" or "a halogen atom" include fluorine, chlorine, and bromine atoms.

Thus, specific examples of the above substituents are as follows. Examples of the lower alkoxy-lower alkyl group include methoxymethyl, methoxyethyl, and ethoxyethyl groups. Examples of the halogen-substituted lower alkyl group include trifluoromethyl, 2,2,2-trifluoroethyl, and 2,2,2-trichloroethyl groups. Examples of the lower alkoxy-lower alkoxy group include methoxyethoxy and ethoxyethoxy groups. Examples of the halogen-substituted lower alkoxy group include difluoromethoxy and 2,2,2-trifluoroethoxy groups. Examples of the lower alkoxycarbonyl-lower alkoxy group include methoxycarbonylmethoxy group. Examples of the aryl lower alkoxy group include phenylmethoxy, phenylethoxy, phenylpropoxy, (4-methoxyphenyl)methoxy, (4-methoxyphenyl)ethoxy, pyridylmethoxy, and pyridylethoxy groups. Examples of the lower alkylthio group include methylthio, ethylthio, and isopropylthio groups. Examples of the lower alkylsulfinyl group include methylsulfinyl, ethylsulfinyl, and isopropylsulfinyl groups. Examples of the lower alkylsulfonyl group include methylsulfonyl, ethylsulfonyl, propylsulfonyl, and isopropylsulfonyl groups. Examples of the lower alkylcarbonyloxy group include butyryloxy, acetoxy, and propionyloxy groups. Examples of the lower alkylsulfonyloxy group include methylsulfonyloxy and ethylsulfonyloxy groups. Examples of the di-lower alkoxyphosphonyloxy group include dimethoxyphosphonyloxy, diethoxyphosphonyloxy, and dipropoxyphosphonyloxy groups. Examples of the lower alkylcarbonyl group include acetyl, propionyl, and butyryl groups. Examples of the mono- or di-lower alkylamino group include methylamino, dimethylamino, and diethylamino groups. Examples of the lower alkylenedioxy group include C1-C6 alkylenedioxy groups such as methylenedioxy, isopropylidenedioxy, ethylpropylidenedioxy, and cyclohexylidenedioxy groups. Examples of the lower alkoxycarbonyl group include methoxycarbonyl, ethoxycarbonyl, and propoxycarbonyl groups. Examples of the mono- or di-lower alkylamino-lower alkyl group include dimethylaminomethyl group.

Examples of the cyclic amino group include morpholino, piperidino, and pyrrolidinyl groups. Examples of the heterocyclic residue include tetrazoline and imidazoyl groups.

In formulas (1) and (3), l is 1 or 2; m is 1 or 2; and n is an integer of 1 to 6. Preferably, m is 1, and n is 2 or 3.

Cyclic diamine derivatives (3) to be employed in the present invention may be converted to the corresponding acid-added salts. Examples of the salts include inorganic acid salts such as hydrochlorides, sulfates, nitrates, and phosphates; and organic acid salts such as methanesulfonates, maleates, fumarates, citrates, tartrates, and malates. Cyclic diamine derivatives (3) may be a non-solvated species or a hydrate or a solvated species formed from a solvent employed in production or purification such as water or alcohol.

According to the method for producing a cyclic diamine derivative (3) from a compound (1), the compound (1) is reacted with a thiol derivative (2a) or (2b) in the presence of a phosphorus compound.

Examples of the phosphorus compound include a phosphine reagent employed in Mitsunobu Reaction; a phosphorus-containing reagent formed of the phosphine reagent with an azo reagent or an ethylenedicarboxylic acid reagent such as dimethyl maleate or N,N,N',N'-tetramethylfumaramide; and a phosphonium ylide reagent.

Examples of preferred modes for carrying out the production method of the present invention include [1] a method including reacting compound (1) with a thiol derivative (2a) in the presence of a phosphine reagent and an azo reagent or an ethylenedicarboxylic acid reagent such as dimethyl maleate or N,N,N',N'-tetramethylfumaramide (Method A), [2] a method including reacting compound (1) with a thiol derivative (2a) in the presence of a phosphonium ylide reagent (Method B), and [3] a method including reacting compound (1) with a thiol derivative (2b) in the presence of a phosphine reagent (Method C).

<Method A>

In Method A, a compound (1), a thiol derivative (2a), and a phosphine reagent are dissolved in a reaction solvent, and an azo reagent or an ethylenedicarboxylic acid reagent is added to the solution. The mixture is allowed to react under argon or nitrogen, at 0° C. to 100° C., preferably at room temperature to 80° C., for 2 hours to 24 hours.

Examples of the phosphine reagents which are employed in the reaction include trialkylphosphines such as trimethylphosphine, triethylphosphine, tripropylphosphine, triisopropylphosphine, tributylphosphine, triisobutylphosphine, and tricyclohexylphosphine and triarylphosphines such as triphenylphosphine and diphenylphosphinopolystyrene. Of these, trimethylphosphine, tributylphosphine, and triphenylphosphine are preferred.

Examples of the azo reagent include diethyl azodicarboxylate (DEAD), diisopropyl azodicarboxylate, di-tert-butyl azodicarboxylate, dibenzyl azodicarboxylate, dimethyl azodicarboxylate, N,N,N',N'-tetramethylazodicarboxamide, 1,1'-azobis(N,N-dimethylformamide) (TMAD), 1,1'-(azodicarbonyl)dipiperidine (ADDP), 1,1'-azobis(N,N-diisopropylformamide) (TIPA), and 1,6-dimethyl-1,5,7-hexahydro-1,4,6,7-tetrazocine-2,5-dione (DHTD). Of these, diethyl azodicarboxylate is preferred.

Examples of the reaction solvent employed in the reaction include dimethylformamide, tetrahydrofuran, dioxane, acetonitrile, nitromethane, acetone, ethyl acetate, benzene, chlorobenzene, toluene, chloroform, and methylene chloride. Of these, dimethylformamide, tetrahydrofuran, dioxane, and acetonitrile are preferred, with dimethylformamide and tetrahydrofuran being more preferred.

<Method B>

In Method B, a compound (1), a thiol derivative (2a), and a phosphonium ylide reagent are dissolved in a reaction solvent. The mixture is allowed to react under argon or nitrogen, at room temperature to 120° C., preferably at 80° C. to 100° C., for 2 hours to 12 hours.

Examples of the phosphonium ylide reagent which is employed in the reaction include alkanoylmethylenetrialkylphosphorane, alkanoylmethylenetriarylphosphorane, alkoxycarbonylmethylenetrialkylphosphorane, alkoxycarbonylmethylenetriarylphosphorane, cyanomethylenetrialkylphosphorane, and cyanomethylenetriarylphosphorane. Examples of the trialkyl moiety include trimethyl, triethyl, tripropyl, triisopropyl, tributyl, triisobutyl, and tricyclohexyl, and examples of the triaryl moiety include triphenyl and diphenylpolystyrene.

Alternatively, in the above reaction, a phosphonium ylide reagent may be generated in the reaction system by adding a compound (1), a thiol derivative (2a), a phosphonium halide reagent, and a base to a reaction solvent.

Examples of the phosphonium halide reagent employable in the alternative method include (cyanomethyl)trialkylphosphonium halide, (cyanomethyl)triarylphosphonium halide, (alkylcarbonylmethyl)trialkylphosphonium halide, (alkylcarbonylmethyl)triarylphosphonium halide, (alkoxycarbonylmethyl)trialkylphosphonium halide, and (alkoxycarbonylmethyl)triarylphosphonium halide.

Notably, among the aforementioned phosphonium halide reagents, (cyanomethyl)trialkylphosphonium halide and (cyanomethyl)triarylphosphonium halide can be prepared by reacting the corresponding trialkylphosphine or triarylphosphine with the corresponding haloacetonitrile (Tetrahedron, vol. 57, pp. 5451-5454, 2001). Similarly, each of the other phosphonium halide reagents can be prepared by reacting the corresponding trialkylphosphine or triarylphosphine with the corresponding alkanoylhalomethyl or alkoxycarbonylhalomethyl.

Examples of trialkylphosphine and triarylphosphine employed herein include the same compounds as shown in Method A. Of these, trimethylphosphine, tributylphosphine, and triphenylphosphine are preferred, with trimethylphosphine being particularly preferred.

Examples of the aforementioned alkanoyl include formyl, acetyl, propionyl, and butyryl. Among them, acetyl and propionyl are preferred. Examples of the alkoxy moiety in the alkoxycarbonyl include methoxy, ethoxy, propoxy, and butoxy. Of these, methoxy, ethoxy, and butoxy are preferred.

As the halogen atom, chlorine, bromine, and iodine are preferred.

Examples of the base include organic bases such as triethylamine, N,N-diisopropylethylamine, 1,4-diazabicyclo[2,2,2]octane (DABCO), 1,8-diazabicyclo[5,4,0]undec-7-ene (DBU), and 1,5-diazabicyclo[4,3,0]non-5-ene (DBN); and inorganic bases such as potassium carbonate, sodium carbonate, cesium carbonate, lithium carbonate, lithium diisopropylamide, and potassium hexamethyldisilazide. Of these, N,N-diisopropylethylamine, potassium carbonate, lithium diisopropylamide, and potassium hexamethyldisilazide are preferred, with N,N-diisopropylethylamine and potassium carbonate being particularly preferred.

Examples of preferred reaction solvents include dioxane, tetrahydrofuran, toluene, benzene, dimethylformamide, dimethyl sulfoxide, acetonitrile, and propionitrile. Among them, propionitrile is particularly preferred.

<Method C>

In Method C, a compound (1), a thiol derivative (2b), and a phosphine reagent are dissolved in a reaction solvent. The mixture is allowed to react under argon or nitrogen, at room temperature to 100° C., preferably at 60° C. to 100° C., for 2 hours to 48 hours.

Examples of phosphine reagents employed herein include the same trialkylphosphine and triarylphosphine as shown in Method A. Specific examples include trimethylphosphine, triethylphosphine, tripropylphosphine, triisopropylphosphine, tributylphosphine, triisobutylphosphine, tricyclohexylphosphine, triphenylphosphine, and diphenylphosphinopolystyrene. Of these, trimethylphosphine, tributylphosphine, and triphenylphosphine are preferred, with trimethylphosphine and triphenylphosphine being particularly preferred.

The compound (1) and the thiol derivatives (2a) and (2b) can be produced through a method disclosed in the aforementioned Patent Document 1 or through a method similar thereto.

EXAMPLES

The present invention next will be described in more detail by way of examples.

Production Example 1

Synthesis of N-[2,4-bis(methylthio)-6-methylpyridin-3-yl]-2-[4-(2-hydroxyethyl)piperazin-1-yl]acetamide 2-Bromo-N-[2,4-bis(methylthio)-6-methylpyridin-3-yl]acetamide (64.16 g, 0.200 mol) was dissolved in acetonitrile (1,200 mL), and 4-(2-hydroxyethyl)piperazine (35.34 g, 0.271 mol) was added thereto. Under cooling with ice, potassium carbonate (37.5 g, 0.271 mol) was added to the mixture. The resultant mixture was returned to room temperature, followed by stirring for 23 hours. The reaction mixture was partitioned with chloroform (1.5 L)-water (1 L), and the organic layer was collected. The aqueous layer was further extracted with chloroform (500 mL×2). The obtained organic layers were combined, followed by washing with saturated brine, drying over sodium sulfate anhydrate, and concentrating under reduced pressure. The obtained residue was recrystallized from ethanol and ether, to thereby yield 60.54 g of N-[2,4-bis(methylthio)-6-methylpyridin-3-yl]-2-[4-(2-hydroxyethyl)piperazin-1-yl]acetamide as colorless needles. The mother liquid was concentrated under reduced pressure, and the residue was recrystallized from ethanol and ether, to thereby yield 11.37 g of N-[2,4-bis(methylthio)-6-methylpyridin-3-yl]-2-[4-(2-hydroxyethyl)piperazin-1-yl]acetamide as colorless needles. The overall yield was 71.91 g (yield 97.2%).

Melting point: 119-120° C. IR (KBr): 3336, 1687, 1564, 1534, 1478 (cm$^{-1}$).

$^1$H-NMR (CDCl$_3$) δ:2.42 (3H, s), 2.50 (3H, s), 2.52 (3H, s), 2.66 (2H, t, J=5.4 Hz), 2.67-2.90 (8H, m), 3.23 (2H, s), 3.69 (2H, t, J=5.4 Hz), 6.67 (1H, s), 8.49 (1H, br.s).

Elemental analysis: as $C_{16}H_{26}N_4O_2S_2$ Calculated: C, 51.86; H, 7.07; N, 15.12; S, 17.31. Found: C, 51.84; H, 7.00; N, 14.92; S, 17.34. EIMS m/z (relative intensity): 370 (M$^+$), 143 (100).

Production Example 2

Synthesis of 4-benzyloxy-2-nitroaniline

4-Amino-3-nitrophenol (25.0 g, 162.21 mmol) was dissolved in acetone (350 mL), and, under stirring with ice-cooling, potassium carbonate (26.9 g, 194.65 mmol) and benzyl bromide (19.7 mL, 165.45 mmol) were added to the solution, followed by stirring at room temperature for 12 hours. The solvent was removed, and water (500 mL) and ethyl acetate (1,000 mL) were added thereto. The resultant organic layer was separated from the mixture. The aqueous layer was further extracted with ethyl acetate (300 mL×2). The obtained organic layers were combined and washed with water (500 mL) and saturated brine (300 mL), followed by drying over sodium sulfate anhydrate. The solvent was removed under reduced pressure, to thereby yield a crude product. The crude product was recrystallized from acetone, to thereby yield 34.3 g of 4-benzyloxy-2-nitroaniline as red needles (yield 86.6%).

Melting point: 141-143° C.

$^1$H-NMR (CDCl$_3$) δ: 5.03 (2H, s), 5.88 (2H, brs), 6.76 (1H, d, J=8.9 Hz), 7.13 (1H, dd, J=8.9, 2.9 Hz), 7.30-7.46 (5H, m), 7.65 (1H, d, J=2.9 Hz).

IR (KBr) cm$^{-1}$: 3477, 3352, 1642, 1593, 1573, 1512. EIMS m/z (relative intensity): 244 (M$^+$), 91 (100).

Production Example 3

Synthesis of 5-benzyloxy-2-mercaptobenzimidazole

4-Benzyloxy-2-nitroaniline (12.0 g, 49.13 mmol) and concentrated hydrochloric acid (12.0 mL) were dissolved in acetic acid (360.0 mL). Under stirring with water-cooling, zinc dust (11.2 g, 172.0 mmol) was gradually added portionwise (5 times) to the mixture. The resultant mixture was returned to room temperature, followed by stirring for 45 minutes. The solvent was removed under reduced pressure. Water (500 mL) was added to the residue, and pH of the solution was adjusted to about 10 through addition of a 5-mol/L aqueous sodium hydroxide solution. To the aqueous solution, chloroform (1000 mL) was added, and the insoluble matter was filtered out by use of Celite. The organic layer of the filtarate was separated from the mixture, and the aqueous layer was further extracted with chloroform (300 mL×2). The obtained organic layers were combined and washed with water (500 mL) and saturated brine (500 mL), followed by drying over sodium sulfate anhydrate. The solvent was removed under reduced pressure, to thereby yield deep red oil (about 11 g). The thus-obatined oil was dissolved in ethanol (500 mL). Potassium O-ethyl dithiocarbonate (11.8 g, 73.70 mmol) was added to the solution, and the mixture was refluxed for 5 hours. After removal of the solvent, water (300 mL) and concentrated hydrochloric acid (40.0 mL) were added to the resultant mixture, and pH of the mixture was adjusted to about 3, followed by extraction with ethyl acetate (400 mL×3). The obtained organic layers were combined and washed with water (500 mL) and saturated brine (300 mL), followed by drying over sodium sulfate anhydrate. The solvent was removed under reduced pressure, and the obtained residue was purified through silica gel column chromatography (chloroform:saturated ammonia-methanol=100:3), to thereby yield 6.02 g of 5-benzyloxy-2-mercaptobenzimidazole as a brown powder (yield 47.8%). The thus-obtained powder was crystallized from hexane-acetone, to thereby yield pale yellow crystalline powder.

Melting point: 239-240° C.

$^1$H-NMR (DMSO-d$_6$) δ: 5.08 (2H, s), 6.75 (1H, d, J=2.3 Hz), 6.79 (1H, ddd, J=8.5, 2.3, 0.9 Hz), 7.02 (1H, d, J=8.5 Hz), 7.26-7.50 (5H, m), 12.4 (1H, brs).

IR (KBr) cm$^{-1}$: 3134, 3093, 1635, 1499, 1453, 1379. EIMS m/e: 256 (M$^+$), 91 (100).

Example 1

Synthesis of 2-[4-[2-(5-benzyloxybenzimidazol-2-ylthio)ethyl]piperazin-1-yl]-N-[2,4-bis(methylthio)-6-methylpyridin-3-yl]acetamide Under argon, N-[2,4-bis(methylthio)-6-methylpyridin-3-yl]-2-[4-(2-hydroxyethyl)piperazin-1-yl]acetamide (1.00 g, 2.70 mmol), 5-benzyloxy-2-mercaptobenzimidazole (2.57 g, 10.0 mmol), and triphenylphosphine (2.50 g, 9.53 mmol) were dissolved in N,N-dimethylformamide (30 mL). To the solution, under cooling with ice, diethyl azodicarboxylate (1.27 mL, 8.07 mmol) was added dropwise, followed by stirring for one hour at the same temperature. Ethyl acetate and 1 mol/L hydrochloric acid were added to the reaction mixture. The aqueous layer was separated from the mixture, and the organic layer was further extracted with 1 mol/L hydrochloric acid. The obtained aqueous layers were combined and adjusted to basic conditions with a 1 mol/L aqueous sodium hydroxide solution, followed by extraction with ethyl acetate. The organic layer was sequentially washed with water and saturated brine, followed by drying over sodium sulfate anhydrate. The solvent was removed under reduced pressure. The thus-obtained residue was purified through silica gel column chromatography (chloroform : saturated ammonia-methanol=20:1), to thereby yield 1.56 g of 2-[4-[2-(5-benzyloxybenzimidazol-2-ylthio)ethyl]piperazin-1-yl]-N-[2,4-bis(methylthio)-6-methylpyridin-3-yl]acetamide as a colorless amorphous product (yield 94.9%).

$^1$H-NMR (CDCl$_3$) δ: 2.42 (3H, s), 2.50 (3H, s), 2.52 (3H, s), 2.68-3.60 (10H, m), 3.20 (2H, t, J=5.2 Hz), 3.32 (2H, s), 5.11 (2H, s), 6.67 (1H, s), 6.93 (1H, dd, J=8.6, 2.4 Hz), 7.20-7.54 (7H, m), 8.42 (1H, brs).

IR (neat) cm$^{-1}$: 3251, 2926, 2822, 1683, 1628, 1564.

Example 2

2-[4-(2-Benzimidazol-2-ylthio)ethylpiperazin-1-yl]-N-[2,4-bis(methylthio)-6-methylpyridin-3-yl]acetamide In an argon atmosphere, N-[2,4-bis(methylthio)-6-methylpyridin-3-yl]-2-[4-(2-hydroxyethyl)piperazin-1-yl]acetamide (1.00 g, 2.70 mmol), 2-mercaptobenzimidazole (1.50 g, 10.0 mmol), and triphenylphosphine (2.50 g, 9.53 mmol) were dissolved in N,N-dimethylformamide (30 mL). Under cooling with ice, diethyl azodicarboxylate (40% w/v toluene solution, 3.50 mL, 8.05 mmol) was added dropwise to the solution, followed by stirring for 1.5 hours at the same temperature. To the reaction solution, ethyl acetate and 1 mol/L hydrochloric acid were added. The aqueous layer was separated from the mixture, and the organic layer was further extracted with 1 mol/L hydrochloric acid. The obtained aqueous layers were combined and made basic by use of 1 mol/L an aqueous sodium hydroxide solution, followed by extraction with ethyl acetate. The organic layer was sequentially washed with water and saturated brine, followed by drying over sodium sulfate anhydrate. The solvent was removed under reduced pressure. The residue was purified through silica gel column chromatography (chloroform:saturated ammonia-methanol=100:3), to thereby yield 1.02 g of 2-[4-(2-benzimidazol-2-ylthio)ethylpiperazin-1-yl]-N-[2,4-bis(methylthio)-6-methylpyridin-3-yl]acetamide as a colorless amorphous product (yield 75.2%). The thus-obtained product was dissolved in ethanol at 80° C., and ether was added thereto. The resultant solution was allowed to stand under cooling with ice. Precipitated crystals were collected, to thereby yield a colorless crystalline powder.

Melting point: 101-102° C. IR (KBr) cm$^{-1}$: 3273, 1672, 1564, 1534, 1488.

$^1$H-NMR (CDCl$_3$): δ 2.42 (3H, s), 2.50 (3H, s), 2.53 (3H, s), 2.71-3.05 (10H, m), 3.23 (2H, t, J=5.4 Hz), 3.35 (2H, s), 6.68 (1H, s), 7.18-7.23 (2H, m), 7.35-7.75 (2H, m), 8.43 (1H, br.), 12.80 (1H, br.).

Elemental analysis: as C$_{23}$H$_{30}$N$_6$OS$_3$.0.2EtOH.0.75H$_2$O Calculated: C, 53.49; H, 6.27; N, 15.99. Found: C, 53.36; H, 5.97; N, 15.73.

Example 3

2-[4-(2-Benzimidazol-2-ylthio)ethylpiperazin-1-yl]-N-[2,4-bis(methylthio)-6-methylpyridin-3-yl]acetamide N-[2,4-Bis(methylthio)-6-methylpyridin-3-yl]-2-[4-(2-hydroxyethyl)piperazin-1-yl]acetamide (370 mg, 1 mmol), 2-mercaptobenzimidazole (150 mg, 1 mmol), and diisopropylethylamine (155 mg, 1.2 mmol) were dissolved in propionitrile (3 mL). Cyanomethyltrimethylphosphonium iodide (267 mg, 1.1 mmol) was added to the solution, and the mixture was stirred for 2 hours at 92° C. The reaction mixture was allowed to stand for cooling. Subsequently, the resultant mixture was poured to water (10 mL), and the solution was extracted with chloroform (10 mL×3). The organic layer was washed with saturated brine, followed by drying over sodium sulfate anhydrate. The solvent was removed under reduced pressure. The obtained residue was purified through silica gel column chromatography (chloroform:saturated ammonia-methanol=100:3), to thereby yield 438 mg of 2-[4-(2-benzimidazol-2-ylthio)ethylpiperazin-1-yl]-N-[2,4-bis(methylthio)-6-methylpyridin-3-yl]acetamide as a colorless amorphous product (yield 87%). The product was treated in a manner similar to that employed in Example 2, to thereby yield a colorless crystalline powder.

Production Example 4

Synthesis of 2-mercapto-5-trifluoromethylbenzoxazole

The procedure (reaction and treatment) of Example 85 described in International Publication WO 98/54153 pamphlet was repeated, except that 4-trifluoromethylphenol was used instead of 2-trifluoromethylphenol, to thereby yield 2-mercapto-5-trifluoromethylbenzoxazole.

$^1$H-NMR (CDCl$_3$): δ 7.42-7.49 (2H, m), 7.53-7.59 (1H, m), 10.6 (1H, brs)

Example 4

Synthesis of 2-[4-[2-(5-trifluoromethylbenzoxazol-2-ylthio)ethyl]piperazin-1-yl]-N-[2,4-bis(methylthio)-6-methylpyridin-3-yl]acetamide The procedure (reaction and treatment) of Example 1 was repeated, except that 5-trifluoromethyl-2-mercaptobenzoxazole was used instead of 5-benzyloxy-2-mercaptobenzimidazole, to thereby yield 2-[4-[2-(5-trifluoromethylbenzoxazol-2-ylthio)ethyl]piperazin-1-yl]-N-[2,4-bis(methylthio)-6-methylpyridin-3-yl]acetamide as colorless crystals.

Melting point: 103-104° C.

$^1$H-NMR (CDCl$_3$): δ 2.42 (3H, s), 2.49 (3H, s), 2.52 (3H, s), 2.60-2.82 (8H, m), 2.86 (2H, t, J=6.8 Hz), 3.21 (2H, s), 3.51 (2H, t, J=6.8 Hz), 6.67 (1H, s), 7.51-7.53 (2H, m), 7.85 (1H, s), 8.55 (1H, s).

Elemental analysis: as C$_{24}$H$_{28}$F$_3$N$_5$O$_2$S$_3$ Calculated: C, 50.42; H, 4.94; N, 12.25, Found: C, 50.59; H, 5.02; N, 12.36.

Production Example 5

Synthesis of 2,4-bis(2,2,2-trifluoroethoxy)-6-methyl-3-nitropyridine 2,4-Dichloro-6-methyl-3-nitropyridine (30 g, 144.9 mmol) was dissolved in 2,2,2-trifluoroethanol (250 mL), and potassium carbonate (50 g, 361.8 mmol) was added to the solution, followed by refluxing for 21 hours. The resultant reaction mixture was dilluted with water, followed by extraction with chloroform. The organic layer was washed with saturated brine, and dried over sodium sulfate anhydrate, followed by concentration under reduced pressure, to thereby yield 2,4-bis (2,2,2-trifluoroethoxy)-6-methyl-3-nitropyridine as a pale yellow solid (45.40 g, 94%).

Melting point: 72.8-73.2° C. IR (KBr): 3432, 3111, 2975, 1610, 1585, 1535 (cm$^{-1}$).

$^1$H-NMR (CDCl$_3$) δ: 2.50 (3H, s), 4.49 (2H, q, J=7.7 Hz), 4.85 (2H, q, J=8.3 Hz), 6.53 (1H, s).

Elemental analysis: as C$_{10}$H$_8$F$_6$N$_2$O$_4$ Calculated: C, 35.94; H, 2.41; N, 8.38, Found: C, 35.94; H, 2.45; N, 8.49.

Production Example 6

Synthesis of 3-amino-2,4-bis(2,2,2-trifluoroethoxy)-6-methylpyridine 2,4-Bis(2,2,2-trifluoroethoxy)-6-methyl-3-nitropyridine (45.00 g, 134.7 mmol) was dissolved in isopropanol (300 mL). Under stirring at 80° C., sodium dithionite (78.00 g, 448.0 mmol) in water (300 mL) was added to the solution. The mixture was further stirred for 15 minutes. Another aliquot of sodium dithionite (16.50 g, 94.8 mmol) in water (51 mL) was further added thereto, followed by stirring for 10 minutes. Yet another aliquot of sodium dithionite (11.10 g, 63.8 mmol) in water (51 mL) was added to the sulution, followed by stirring for 10 minutes. After completion of reaction, a 4-mol/L aqueous sulfuric acid solution (201 mL) was added to the reaction mixture, followed by stirring for 30 minutes at 90° C. The resultant mixture was allowed to stand for cooling and, under ice-water, 28% aqueous ammonia (360 mL) was added thereto, followed by stirring for 30 minutes. The reaction mixture was dilluted with water, and subjected to extraction with chloroform. The organic layer was washed with saturated brine, followed by drying over sodium sulfate anhydrate and concentration under reduced pressure, to thereby yield crystals. The thus-obtained crystals were recrystallized from hexane, to thereby yield 3-amino-2,4-bis (2,2,2-trifluoroethoxy)-6-methylnitropyridine as pale yellow needles (32.91 g, 80%).

Melting point: 53.5-53.8° C. IR (KBr): 3453, 3314, 2968, 1603, 1505, 1456 (cm$^{-1}$).

$^1$H-NMR (CDCl$_3$) δ: 2.34 (3H, s), 3.66 (2H, br. s), 4.39 (2H, q, J=8.0 Hz), 4.79 (2H, q, J=8.6 Hz), 6.35 (1H, s).

Elemental analysis: as C$_{10}$H$_{10}$F$_6$N$_2$O$_2$.0.55H$_2$O Calculated: C, 38.24; H, 3.56; N, 8.92, Found: C, 37.96; H, 3.19; N, 8.94

Production Example 7

Production of 2-bromo-N-[2,4-bis(2,2,2-trifluoroethoxy)-6-methylpyridin-3-yl]acetamide:

3-Amino-2,4-bis(2,2,2-trifluoroethyloxy)-6-methylnitropyridine (42.29 g, 139.0 mmol) was dissolved in dichloromethane (600 mL). To the soluiton, N,N-dimethylaniline (20.46 g, 168.8 mmol) was added. Bromoacetyl bromide (28.73 g, 142.3 mmol) in dichloromethane (100 mL) was added to the mixture, while the mixture was cooled with ice-water and stirred. The mixture was further stirred for 10 minutes. The reaction mixture was dilluted with water, followed by extraction with chloroform. The organic layer was washed with saturated brine, followed by drying over sodium sulfate anhydrate and concentration under reduced pressure, to thereby form crystals. The crystals were recrystallized from chloroform and n-hexane, to thereby yield 2-bromo-N-[2,4-bis(2,2,2-trifluoroethoxy)-6-methylpyridin-3-yl]acetamide as colorless needles (50.25 g, 85%).

Melting point: 152.8-154.0° C. IR (KBr): 3250, 3053, 1677, 1597, 1541, 1456 (cm$^{-1}$).

$^1$H-NMR (CDCl$_3$)δ: 2.43 (3H, s), 4.02 (2H, s), 4.42 (2H, q, J=7.9 Hz), 4.78 (2H, q, J=8.5 Hz), 6.47 (1H, s), 7.49 (1H, br s).

Elemental analysis: as C$_{12}$H$_{11}$BrF$_6$N$_2$O$_3$ Calculated: C, 33.90; H, 2.61; N, 6.59, Found: C, 34.13; H, 2.66; N, 6.65.

Production Example 8

Synthesis of N-[2,4-bis(2,2,2-trifluoroethoxy)-6-methylpyridin-3-yl]-2-[4-(2-hydroxyethyl)piperazin-1-yl]acetamide 1-(2-Hydroxyethyl)piperazine (1.95 g, 15.0 mmol) and 2-bromo-N-[2,4-bis(2,2,2-trifluoroethoxy)-6-methylpyridin-3-yl]acetamide (5.00 g, 12.5 mmol) were dissolved in acetonitrile (30 mL). Potassium carbonate (2.25 g, 16.3 mmol) was added to the solution, followed by stirring for 5 hours at room temperature. The reaction mixture was dilluted with water, followed by extraction with ethyl acetate. The organic layer was sequentially washed with water and saturated brine, followed by drying over sodium sulfate anhydrate and concentration under reduced pressure. The obtained residue was purified through silica gel column chromatography (eluent: ammonia-saturated methanol/chloroform=1/20), to thereby yield 5.40 g of N-[2,4-bis(2,2,2-trifluoroethoxy)-6-methylpyridin-3-yl]-2-[4-(2-hydroxyethyl)piperazin-1-yl]acetamide as colorless crystals (yield 91%).

Melting point: 117-118° C.

$^1$H-NMR (CDCl$_3$) δ: 2.42 (3H, s), 2.48-2.82 (8H, m), 2.57 (2H, t, J=5.3 Hz), 3.17 (2H, s), 3.63 (2H, t, J=5.3 Hz), 4.41 (2H, q, J=8.0 Hz), 4.75 (2H, q, J=8.5 Hz), 6.47 (1H, s), 8.38 (1H, brs).

Production Example 9

Synthesis of 5,6-difluoro-2-mercaptobenzimidazole 3,4-Difluoro-6-nitroaniline (5.75 g, 33.03 mmol) was dissolved in acetic acid (100 mL) and concentrated hydrochloric acid (2.3 mL). While the solution was vigorously stirred on an ice bath, zinc dust (6.91 g, 105.6 mmol) was added to the solution over a period of 10 minutes. The reaction mixture was stirred at the same temperature for 20 minutes and at room temperature for 130 minutes. On an ice bath, zinc dust (1.20 g, 18.35 mmol) was added to the reaction mixture over 5 minutes, followed by stirring for 30 minutes at the same temperature. The reaction mixture was concentrated under reduced pressure. The obtained residue was neutralized with a saturated aqueous sodium bicarbonate solution, followed by filtration by use of Celite. The filtrate was extracted with chloroform, and the organic layer was washed with saturated brine. After washing, the organic layer was dried over sodium sulfate anhydrate, followed by concentration under reduced pressure, to thereby yield a brown oil (4.73 g).

The brown oil was dissolved in ethanol (200 mL). Potassium xanthate (15.75 g, 98.25 mmol) was added to the solution, followed by refluxing for 14 hours. The reaction mixture was concentrated under reduced pressure, and the obtained residue was extracted with ethyl acetate-1 mol/L hydrochloric acid. The organic layer was washed with saturated brine, followed by drying over sodium sulfate anhydrate and concentration under reduced pressure. The thus-obtained residue was recrystallized from chloroform and n-hexane, to thereby yield 5,6-difluoro-2-mercaptobenzimidazole as a pale brown powder (5.58 g, 2 steps 91%).

Melting point: 296-298° C.

Example 5

Synthesis of 2-[4-[2-(5,6-difluorobenzimidazol-2-ylthio)ethyl]piperazin-1-yl]-N-[2,4-bis(2,2,2-trifluoroethoxy)-6-methylpyridin-3-yl]acetamide The procedure (reaction and treatment) of Example 1 was repeated, except that 5,6-difluoro-2-mercaptobenzimidazole was used instead of 5-benzyloxy-2-mercaptobenzimidazole and that N-[2,4-bis(2,2,2-trifluoroethoxy)-6-methylpyridin-3-yl]-2-[4-(2-hydroxyethyl)piperazin-1-yl]acetamide was used instead of N-[2,4-bis(methylthio)-6-methylpyridin-3-yl]-2-[4-(2-hydroxyethyl)piperazin-1-yl]acetamide, to thereby yield 2-[4-[2-(5,6-difluorobenzimidazol-2-ylthio) ethyl]piperazin-1-yl]-N-[2,4-bis(2,2,2-trifluoroethoxy)-6-methylpyridin-3-yl]acetamide as colorless crystals.

Melting point: 191-192° C. IR (KBr) cm$^{-1}$: 3275, 1686, 1604, 1591, 1509.

$^1$H-NMR (DMSO-d$_6$) δ: 2.38 (3H, s), 2.42-2.62 (8H, m), 2.67 (2H, t, J=6.7 Hz), 3.30 (2H, s), 3.40 (2H, t, J=6.7 Hz), 4.82 (2H, q, J=8.8 Hz), 4.90 (2H, q, J=8.8 Hz), 6.91 (1H, s), 7.47 (2H, m), 8.77 (1H, s), 12.82 (1H, brs)

Elemental analysis: as $C_{25}H_{26}F_8N_6O_3S$ Calculated: C, 46.73; H, 4.08; N, 13.08 Found: C, 46.55; H, 4.12; N, 12.94

Example 6

Synthesis of 2-[4-[2-(5,6-difluorobenzimidazol-2-ylthio)ethyl]piperazin-1-yl]-N-[2,4-bis(2,2,2-trifluoroethoxy)-6-methylpyridin-3-yl]acetamide The procedure (reaction and treatment) of Example 1 was repeated, except that 5,6-difluoro-2-mercaptobenzimidazole was used instead of 5-benzyloxy-2-mercaptobenzimidazole and that N-[2,4-bis(2,2,2-trifluoroethoxy)-6-methylpyridin-3-yl]-2-[4-(2-hydroxyethyl)piperazin-1-yl]acetamide was used instead of N-[2,4-bis(methylthio)-6-methylpyridin-3-yl]-2-[4-(2-hydroxyethyl)piperazin-1-yl]acetamide, to thereby yield 2-[4-[2-(5,6-difluorobenzimidazol-2-ylthio) ethyl]piperazin-1-yl]-N-[2,4-bis(2,2,2-trifluoroethoxy)-6-methylpyridin-3-yl]acetamide as colorless crystals.

Melting point: 152-153° C. IR (ATR) cm$^{-1}$: 2951, 2820, 2362, 1698, 1591, 1508.

$^1$H-NMR (CDCl$_3$) δ: 2.43 (3H, s), 2.65-2.97 (8H, m), 3.01 (2H, t, J=5.0 Hz), 3.23 (2H, t, J=5.0 Hz), 3.31 (2H, s), 4.42 (2H, q, J=8.0 Hz), 4.75 (2H, q, J=8.5 Hz), 6.48 (1H, s), 7.06-7.24 (2H, m), 7.41-7.65 (2H, m), 8.26 (1H, s).

Elemental analysis: as $C_{25}H_{28}F_6N_6O_3S$ Calculated: C, 49.50; H, 4.65; N, 13.85; F, 18.79 Found: C, 49.48; H, 4.71; N, 13.92; F, 18.79

Example 7

Synthesis of 2-[4-[2-(benzoxazol-2-ylthio)ethyl] piperazin-1-yl]-N-[2,4-bis(2,2,2-trifluoroethoxy)-6-methylpyridin-3-yl]acetamide The procedure (reaction and treatment) of Example 1 was repeated, except that 2-mercaptobenzoxazole was used instead of 5-benzyloxy-2-mercaptobenzimidazole and that N-[2,4-bis(2,2,2-trifluoroethoxy)-6-methylpyridin-3-yl]-2-[4-(2-hydroxyethyl)piperazin-1-yl]acetamide was used instead of N-[2,4-bis(methylthio)-6-methylpyridin-3-yl]-2-[4-(2-hydroxyethyl)piperazin-1-yl]acetamide, to thereby yield 2-[4-[2-(benzoxazol-2-ylthio)ethyl]piperazin-1-yl]-N-[2,4-bis(2,2,2-trifluoroethoxy)-6-methylpyridin-3-yl]acetamide as colorless crystals.

Melting point: 141-142° C.

$^1$H-NMR (CDCl$_3$) δ: 2.42 (3H, s), 2.54-2.76 (8H, m), 2.84 (2H, t, J=6.9 Hz), 3.15 (2H, s), 3.49 (2H, t, J=6.9 Hz), 4.41 (2H, q, J=8.0 Hz), 4.75 (2H, q, J=8.5 Hz), 6.46 (1H, s), 7.25-7.35 (2H, m), 7.43 (1H, d, J=7.8 Hz), 7.59 (1H, d, J=7.8 Hz), 8.38 (1H, s).

Production Example 10

Synthesis of methyl 2,6-dimethyl-4-trifluoromethylpyridine-3-carboxylate 1,1,1-Trifluoro-2,4-pentanedione (25.01 g, 135.3 mmol) was dissolved in acetonitrile (230 mL). Methyl 3-aminocrotonate (15.57 g, 135.2 mmol) was added to the solution, followed by refluxing for 20 hours. The reaction mixture was allowed to stand for cooling, followed by concentration under reduced pressure. The residue was purified through silica gel column chromatography (eluent: n-hexane/acetone=10/1), to thereby yield methyl 2,6-dimethyl-4-trifluoromethylpyridine-3-carboxylate as a yellow oil (22.30 g, 71%).

$^1$H-NMR (CDCl$_3$) δ: 2.59 (3H, s), 2.63 (3H, s), 3.95 (3H, s), 7.26 (1H, s).

Production Example 11

Synthesis of 2,6-dimethyl-4-trifluoromethylpyridine-3-carboxylic acid hydrochloride Methyl 2,6-dimethyl-4-trifluoromethylpyridine-3-carboxylate (23.30 g, 99.9 mmol) was dissolved in ethanol (50 mL). A 5-mol/L aqueous potassium hydroxide solution (50 mL, 250 mmol) was added to the solution, followed by refluxing for 2 days. The reaction mixture was allowed to stand for cooling, and concentrated hydrochloric acid (15 mL) was added to the resultant mixture, followed by concentration under reduced pressure. To the obtained residue, ethanol was added, and the mixture was heated for dissolution. Insoluble matter was removed through filtration, and the filtrate was concentrated under reduced pressure. Ether was added to the thus-obtained residue, and the solid was collected through filtration, to thereby yield 2,6-dimethyl-4-trifluoromethylpyridine-3-carboxylic acid hydrochloride as a colorless powder (25.24 g, 99%).

$^1$H-NMR (DMSO-d$_6$) δ: 2.53 (3H, s), 2.57 (3H, s), 7.57 (1H, s).

Production Example 12

Synthesis of 3-tert-butoxycarbonylamino-2,6-dimethyl-4-trifluoromethylpyridine 2,6-Dimethyl-4-trifluoromethylpyridine-3-carboxylic acid hydrochloride (23.17 g, 90.6 mmol) was suspended in tert-butanol (175 mL). Diphenylphosphonic azide (35.25 g, 128.1 mmol) and triethylamine (31.36 g, 309.9 mmol) were added to the suspension, followed by refluxing for 3 hours. The reaction mixture was allowed to stand for cooling. Subsequently, water (100 mL) was added to the mixture, followed by extraction with chloroform. The obtained organic layer was dried over sodium sulfate anhydrate, followed by concentration under reduced pressure. The obtained residue was purified through silica gel column chromatography (eluent: n-hexane: acetone=10:1), to thereby yield 3-tert-butoxycarbonylamino-2,6-dimethyl-4-trifluoromethylpyridine as a pale yellow oil (18.01 g, 68%).

$^1$H-NMR (CDCl$_3$) δ: 1.51 (9H, s), 2.56 (3H, s), 2.59 (3H, s), 6.10 (1H, brs), 7.24 (1H, s).

Production Example 13

Synthesis of 3-amino-2,6-dimethyl-4-trifluoromethylpyridine dihydrochloride 3-tert-Butoxycarbonylamino-2,6-dimethyl-4-trifluoromethylpyridine(21.12 g, 72.8 mmol) was dissolved in methanol (70 mL). 10% hydrochloric acid in methanol (140 mL) was added to the solution, followed by stirring for 12 hours at 60° C. The reaction mixture was concentrated under reduced pressure, and the residue was suspended in a solvent mixture of ethyl acetate-ether, followed by collection through filtration and washing with ether, to thereby yield 3-amino-2,6-dimethyl-4-trifluoromethylpyridine dihydrochloride as a colorless powder (15.64 g, 82%).

$^1$H-NMR (DMSO-d$_6$) δ: 2.53 (3H, s), 2.59 (3H, s), 4.50 (2H, br), 6.44 (2H, br), 7.70 (1H, s).

Production Example 14

Synthesis of 2-bromo-N-(2,6-dimethyl-4-trifluoromethylpyridin-3-yl)acetamide

3-Amino-2,6-dimethyl-4-trifluoromethylpyridine dihydrochloride (15.60 g, 59.30 mmol) was dissolved in methanol (100 mL). In an ice bath, saturated ammonia in methanol (300 mL) was added to the solution, followed by sufficiently mixing to form a uniform mixture. The reaction mixture was extracted with chloroform-water, and the organic layer was washed with saturated brine, followed by drying over sodium sulfate anhydrate and concentration under reduced pressure. The thus-obtained residue was suspended in dichloromethane (200 mL), and N,N-dimethylaniline (10.80 g, 89.12 mmol) was added thereto. Under stirring on an ice bath, bromoacetyl bromide (15.52 g, 76.90 mmol) in dichloromethane (40 mL) was added dropwise to the mixture, followed by stirring for 2 hours at room temperature. The reaction mixture was concentrated under reduced pressure. The thus-obtained residue was purified through silica gel column chromatography (eluent: n-hexane/acetone=10/1→4/1→3/1), followed by recrystallization from ethyl acetate-hexane, to thereby yield 2-bromo-N-(2,6-dimethyl-4-trifluoromethylpyridin-3-yl)acetamide as colorless needles (17.68 g, 96%).

$^1$H-NMR (CDCl$_3$) δ: 2.51 (3H, s), 2.62 (3H, s), 4.06 (2H, s), 7.29 (1H, s), 7.93 (1H, brs).

Production Example 15

Synthesis of N-[2,6-dimethyl-4-trifluoromethylpyridin-3-yl]-2-[4-(2-hydroxyethyl)piperazin-1-yl]acetamide The procedure (reaction and treatment) of Production Example 8 was repeated, except that 2-bromo-N-[2,6-dimethyl-4-trifluoromethylpyridin-3-yl]acetamide was used instead of 2-bromo-N-[2,4-bis(2,2,2-trifluoroethoxy)-6-methylpyridin-3-yl]acetamide, to thereby yield N-[2,6-dimethyl-4-trifluoromethylpyridin-3-yl]-2-[4-(2-hydroxyethyl)piperazin-1-yl]acetamide as colorless crystals.

Example 8

Synthesis of 2-[4-[2-(benzothiazol-2-ylthio)ethyl]piperazin-1-yl]-N-[2,6-dimethyl-4-trifluoromethylpyridin-3-yl]acetamide The procedure (reaction and treatment) of Example 1 was repeated, except that 2-mercaptobenzothiazole was used instead of 5-benzyloxy-2-mercaptobenzimidazole and that N-[2,6-dimethyl-4-trifluoromethylpyridin-3-yl]-2-[4-(2-hydroxyethyl)piperazin-1-yl]acetamide was used instead of N-[2,4-bis(methylthio)-6-methylpyridin-3-yl]-2-[4-(2-hydroxyethyl)piperazin-1-yl]acetamide, to thereby yield 2-[4-[2-(benzothiazol-2-ylthio)ethyl]piperazin-1-yl]-N-[2,6-dimethyl-4-trifluoromethylpyridin-3-yl]acetamide as colorless crystals.

Melting point: 107-108° C. IR (KBr) cm$^{-1}$: 3291, 1816, 1699, 1602, 1575, 1485.

$^1$H-NMR (DMSO-d$_6$) δ: 2.34 (3H, s), 2.53 (3H, s), 2.53-2.60 (8H, m), 2.74 (2H, t, J=6.8 Hz), 3.13 (2H, s), 3.53 (2H, t, J=6.8 Hz), 7.35 (1H, td, J=7.3, 1.2 Hz), 7.45 (1H, td, J=7.3, 1.2 Hz), 7.83 (1H, dd, J=7.3, 1.2 Hz), 7.99 (1H, dd, J=7.3, 1.2 Hz), 9.46 (1H, s).

Elemental analysis: as $C_{23}H_{26}F_3N_5OS_2$ Calculated: C, 54.21; H, 5.14; N, 13.74; F, 11.18. Found: C, 54.23; H, 5.21; N, 13.56; F, 11.16.

Production Example 16

Synthesis of 2-[(2-methoxyethyl)oxy]-6-methyl-4-methylthio-3-nitropyridine

2-Chloro-6-methyl-4-methylthio-3-nitropyridine (2.80 g, 12.81 mmol) was dissolved in 2-methoxyethanol (40 mL). Potassium carbonate (1.90 g, 13.75 mmol) was added to the solution, followed by stirring for 5 hours at 60° C. The mixture was allowed to stand for cooling. Subsequently, the resultant mixture was extracted with ether-water, and the organic layer was washed with saturated brine, followed by drying sodium sulfate anhydrate and concentration under reduced pressure. The obtained residue was purified through silica gel column chromatography [(1) (eluent: n-hexane/ethyl acetate=4/1→n-hexane/ethyl acetate=2/1), (2) (eluent: chloroform)], to thereby yield 2-[(2-methoxyethyl)oxy]-6-methyl-4-methylthio-3-nitropyridine as a pale yellow oil (2.21 g, 67%).

$^1$H-NMR (CDCl$_3$) δ: 2.46 (3H, s), 2.48 (3H, s), 3.41 (3H, s), 3.73 (2H, t, J=4.9 Hz), 4.57 (2H, t, J=4.9 Hz), 6.64 (1H, s).

Production Example 17

Synthesis of 2-[(2-methoxyethyl)oxy]-6-methyl-4-methylsulfinyl-3-nitropyridine

2-[(2-methoxyethyl)oxy]-6-methyl-4-methylthio-3-nitropyridine (2.00 g, 7.74 mmol) was dissolved in dichloromethane (25 mL). m-Chloroperbenzoic acid (60%, 5.0 g, 17.38 mmol) was added to the solution, followed by stirring at room temperature for 12 hours. Saturated aqueous sodium sulfite was added to the reaction mixture, followed by stirring for 1.5 hours so that excessive m-chloroperbenzoic acid was deactivated. The organic layer was washed with saturated brine, followed by drying over sodium sulfate anhydrate and concentration under reduced pressure. The obtained residue was recrystallized from ether, to thereby yield 2-[(2-methoxyethyl)oxy]-6-methyl-4-methylsulfinyl-3-nitropyridine as colorless crystals (1.93 g, 91%).

$^1$H-NMR (CDCl$_3$) δ: 2.60 (3H, s), 3.27 (3H, s), 3.40 (3H, s), 3.73 (2H, t, J=4.8 Hz), 4.62 (2H, t, J=4.8 Hz), 7.33 (1H, s).

Production Example 18

Synthesis of 2-[(2-methoxyethyl)oxy]-6-methyl-3-nitro-4-[(2,2,2-trifluoroethyl)oxy]pyridine 2-[(2-Methoxyethyl)oxy]-6-methyl-4-methylsulfinyl-3-nitropyridine (1.73 g, 6.31 mmol) was dissolved in 2,2,2-trifluoroethanol (15 mL). Sodium hydride (55% in oil, 600 mg, 13.75 mmol) was added to the solution, followed by refluxing for one hour. The resultant solution was allowed to stand for cooling. Subsequently, the solution was extracted with chloroform-water. The organic layer was washed with saturated brine, followed by drying over sodium sulfate anhydrate and concentration under reduced pressure. The obtained residue was purified through silica gel column chromatography (eluent: n-hexane/ethyl acetate=5/1→n-hexane/ethyl acetate=3/1), to thereby yield 2-[(2-methoxyethyl)oxy]-6-methyl-3-nitro-4-[(2,2,2-trifluoroethyl)oxy]pyridine as a pale yellow solid (1.77 g, 91%).

$^1$H-NMR (CDCl$_3$) δ: 2.46 (3H, s), 3.40 (3H, s), 3.71 (2H, t, J=4.9 Hz), 4.46 (2H, q, J=8.0 Hz), 4.56 (2H, t, J=4.9 Hz), 6.42 (1H, s).

Production Example 19

Synthesis of 3-amino-2-[(2-methoxyethyl)oxy]-6-methyl-4-[(2,2,2-trifluoroethyl)oxy]pyridine 2-[(2-Methoxyethyl)oxy]-6-methyl-3-nitro-4-[(2,2,2-trifluoroethyl)oxy]pyridine (1.65 g, 5.32 mmol) was dissolved in a mixed solvent of dioxane (30 mL)-methanol (30 mL). Raney nickel (ethanol suspension, 3 mL) was added to the solution. In a hydrogen atmosphere, the mixture was stirred at room temperature for 26 hours. The reaction mixture was subjected to filtration, and the filtrate was concentrated under reduced pressure, to thereby yield 3-amino-2-[(2-methoxyethyl)oxy]-6-methyl-4-[(2,2,2-trifluoroethyl)oxy]pyridine as a pale yellow oil (1.49 g, 99%).

$^1$H-NMR (DMSO-d$_6$) δ: 2.48 (3H, s), 3.42 (3H, s), 3.76 (2H, t, J=3.6 Hz), 4.43 (2H, q, J=7.6 Hz), 4.66 (2H, br), 6.36 (1H, s).

Production Example 20

Synthesis of 2-bromo-N-[2-[(2-methoxyethyl)oxy]-6-methyl-4-[(2,2,2-trifluoroethyl)oxy]pyridin-3-yl]acetamide 3-Amino-2-[(2-methoxyethyl)oxy]-6-methyl-4-[(2,2,2-trifluoroethyl)oxy]pyridine (1.39 g, 4.96 mmol) was dissolved in dichloromethane (15 mL). N,N-dimethylaniline (0.76 g, 6.27 mmol) was added to the solution. Under stirring on an ice bath, bromoacetyl bromide (1.16 g, 5.75 mmol) in dichloromethane (5 mL) was added dropwise to the mixture, followed by stirring at the same temperature for 30 minutes. The reacion mixture was directly subjected to silica gel column chromatography (eluent: n-hexane/ethyl acetate=5/1→n-hexane/acetone=1/1) for purification, to thereby yield 2-bromo-N-[2-[(2-methoxyethyl)oxy]-6-methyl-4-[(2,2,2-trifluoroethyl)oxy]pyridin-3-yl]acetamide as a colorless solid (1.98 g, 99%).

$^1$H-NMR (CDCl$_3$) δ: 2.41 (3H, s), 3.42 (3H, s), 3.72 (2H, t, J=4.8 Hz), 4.00 (2H, s), 4.40 (2H, q, J=8.1 Hz), 4.50 (2H, t, J=4.8 Hz), 6.39 (1H, s), 7.54 (1H, brs).

Production Example 21

Synthesis of N-[2-(2-methoxyethoxy)-4-(2,2,2-trifluoroethoxy)-6-methylpyridin-3-yl]-2-[4-(2-hydroxyethyl)piperazin-1-yl]acetamide The procedure (reaction and treatment) of Production Example 8 was repeated, except that 2-bromo-N-[2-(2-methoxyethoxy)-4-(2,2,2-trifluoroethoxy)-6-methylpyridin-3-yl] acetamide was used instead of 2-bromo-N-[2,4-bis(2,2,2-trifluoroethoxy)-6-methylpyridin-3-yl]acetamide, to thereby yield N-[2-(2-methoxyethoxy)-4-(2,2,2-trifluoroethoxy)-6methylpyridin-3-yl]-2-[4-(2-hydroxyethyl)piperazin-1-yl]acetamide as colorless crystals.

Example 9

Synthesis of 2-[4-[2-(benzoxazol-2-ylthio)ethyl]piperazin-1-yl]-N-[2-(2-methoxyethoxy)-4-(2,2,2-trifluoroethoxy)-6-methylpyridin-3-yl]acetamide The procedure (reaction and treatment) of Example 1 was repeated, except that 2-mercaptobenzoxazole was used instead of 5-benzyloxy-2-mercaptobenzimidazole and that N-[2-(2-methoxyethoxy)-4-(2,2,2-trifluoroethoxy)-6-methylpyridin-3-yl]-2-[4-(2-hydroxyethyl)piperazin-1-yl]acetamide was used instead of N-[2,4-bis(methylthio)-6-methylpyridin-3-yl]-2-[4-(2-hydroxyethyl)piperazin-1-yl] acetamide, to thereby yield 2-[4-[2-(benzoxazol-2-ylthio) ethyl]piperazin-1-yl]-N-[2-(2-methoxyethoxy)-4-(2,2,2-trifluoroethoxy)-6-methylpyridin-3-yl]acetamide as colorless crystals.

$^1$H-NMR (DMSO-d$_6$) δ: 2.35 (3H, s), 2.43-2.60 (8H, m), 2.73 (2H, t, J=6.4 Hz), 3.00 (2H, s), 3.26 (3H, s), 3.50 (2H, t, J=6.4 Hz), 3.58 (2H, t, J=4.6 Hz), 4.32 (2H, t, J=4.6 Hz), 4.78 (2H, q, J=8.8 Hz), 6.78 (1H, s), 7.27-7.35 (2H, m), 7.59-7.65 (2H, m), 8.63 (1H, brs).

The invention claimed is:

1. A method for producing a cyclic diamine derivative represented by formula (3)

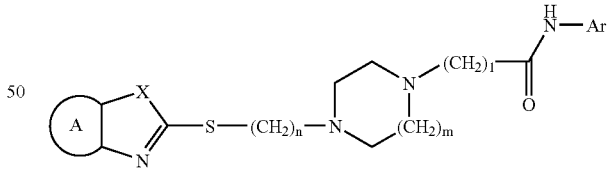

(3)

or a salt thereof, comprising:
reacting a compound represented by formula (1):

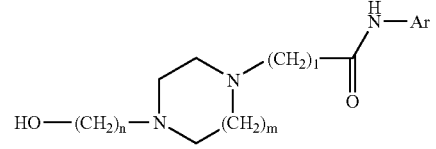

(1)

with a thiol derivative represented by formula (2a) or (2b):

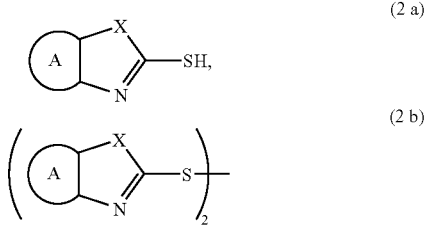

in the presence of a phosphorus compound, wherein
Ar represents a phenyl group, a pyridyl group, or a pyrimidinyl group, any of which may have a substituent; X represents NH, S, or O; ring A represents a benzene ring or a pyridine ring, which may have a substituent; l represents an integer of 1 or 2; m represents an integer of 1 or 2; and n represents an integer of 1 to 6, and
the phosphorus compound is a reagent selected from the group consisting of a phosphine reagent, a phosphorus reagent formed of a phosphine and an azo compound, a phosphorus reagent formed of a phosphine and an ethylenedicarboxylic acid and a phosphonium ylide reagent.

2. The method according to claim 1, wherein the compound represented by formula (1), the thiol derivative represented by formula (2a), and a phosphine reagent are dissolved in a solvent and an azo compound is added for the reacting.

3. The method according to claim 2, wherein the phosphine is selected from the group consisting of trimethylphosphine, triethylphosphine, tripropylphosphine, triisopropylphosphine, tributylphosphine, triisobutylphosphine, tricyclohexylphosphine, triphenylphosphine and diphenylphosphinopolystyrene.

4. The method according to claim 2, wherein the azo compound is selected from the group consisting of diethyl azodicarboxylate (DEAD), diisopropyl azodicarboxylate, di-tert-butyl azodicarboxylate, dibenzyl azodicarboxylate, dimethyl azodicarboxylate, N,N,N',N'-tetramethylazodicarboxamide, 1,1'-azobis(N,N-dimethylformamide) (TMAD), 1,1'-(azodicarbonyl)dipiperidine (ADDP), 1,1'-azobis(N,N-diisopropylformamide) (TIPA), and 1,6-dimethyl-1,5,7-hexahydro-1,4,6,7-tetrazocine-2,5-dione (DHTD).

5. The method according to claim 2, wherein the solvent is selected from the group consisting of dimethylformamide, tetrahydrofuran, dioxane, acetonitrile, nitromethane, acetone, ethyl acetate, benzene, chlorobenzene, toluene, chloroform, and methylene chloride.

6. The method according to claim 1, wherein the compound represented by formula (1), the thiol derivative represented by formula (2a), and a phosphine are dissolved in a solvent and an ethylenedicarboxylic acid is added for the reacting.

7. The method according to claim 6, wherein the ethylenedicarboxylic acid is dimethyl maleate or N, N, N', N'-tetramethylfumaramide.

8. The method according to claim 6, wherein the phosphine is selected from the group consisting of trimethylphosphine, triethylphosphine, tripropylphosphine, triisopropylphosphine, tributylphosphine, triisobutylphosphine, tricyclohexylphosphine, triphenylphosphine and diphenylphosphinopolystyrene.

9. The method according to claim 6, wherein the solvent is selected from the group consisting of dimethylformamide, tetrahydrofuran, dioxane, acetonitrile, nitromethane, acetone, ethyl acetate, benzene, chlorobenzene, toluene, chloroform, and methylene chloride.

10. The method according to claim 1, wherein the compound represented by formula (1), the thiol derivative represented by formula (2a), and a phosphonium ylide reagent are dissolved in a solvent for the reacting.

11. The method according to claim 10, wherein the phosphonium ylide is one selected from the group consisting of an alkanoylmethylenetrialkylphosphorane, an alkanoylmethylenetriarylphosphorane, an alkoxycarbonylmethylenetrialkylphosphorane, an alkoxycarbonylmethylenetriarylphosphorane, a cyanomethylenetrialkylphosphorane, and a cyanomethylenetriarylphosphorane.

12. The method according to claim 10, wherein the phosphonium ylide reagent is generated in the reacting from a phosphonium halide and a base.

13. The method according to claim 12, wherein the phosphonium halide is selected from the group consisting of (cyanomethyl)trialkylphosphonium halide, (cyanomethyl)triarylphosphonium halide, (alkylcarbonylmethyl)trialkylphosphonium halide, (alkylcarbonylmethyl)triarylphosphonium halide, (alkoxycarbonylmethyl)trialkylphosphonium halide, and (alkoxycarbonylmethyl)triarylphosphonium halide.

14. The method according to claim 12, wherein the base is selected from the group consisting of triethylamine, N,N-diisopropylethylamine, 1,4-diazabicyclo[2,2,2]octane (DABCO), 1,8-diazabicyclo[5,4,0]undec-7-ene (DBU), 1,5-diazabicyclo[4,3,0]non-5-ene (DBN), potassium carbonate, sodium carbonate, cesium carbonate, lithium carbonate, lithium diisopropylamide, and potassium hexamethyldisilazide.

15. The method according to claim 12, wherein the solvent is selected from the group consisting of dioxane, tetrahydrofuran, toluene, benzene, dimethylformamide, dimethyl sulfoxide, acetonitrile, and propionitrile.

16. The method according to claim 1, wherein the compound represented by formula (1), the thiol derivative represented by formula (2b), and a phosphine are dissolved in a solvent for the reacting.

17. The method according to claim 16, wherein the phosphine is selected from the group consisting of trimethylphosphine, triethyiphosphine, tripropylphosphine, triisopropylphosphine, tributyiphosphine, triisobutylphosphine, tricyclohexyiphosphine, triphenyiphosphine, and diphenyiphosphinopolystyrene.

18. The method according to claim 1, wherein the reacting is under argon or nitrogen.

* * * * *

UNITED STATES PATENT AND TRADEMARK OFFICE
CERTIFICATE OF CORRECTION

PATENT NO. : 7,459,552 B2
APPLICATION NO. : 10/558197
DATED : December 2, 2008
INVENTOR(S) : Kimiyuki Shibuya et al.

It is certified that error appears in the above-identified patent and that said Letters Patent is hereby corrected as shown below:

Col. 20,
In line 52 of Claim 17, change "triethyiphosphine" to --triethylphosphine--
In line 53 of Claim 17, change "tributyiphosphine" to --tributylphosphine--
In line 54 of Claim 17, change "tricyclohexiphosphine" to --tricyclohexlphosphine--, change "triphenyiphosphine" to --triphenylphosphine--, and change "diphenyi-" to --diphenyl- --

Signed and Sealed this

Twenty-fourth Day of February, 2009

JOHN DOLL
*Acting Director of the United States Patent and Trademark Office*